(12) United States Patent
Michaels et al.

(10) Patent No.: US 9,072,462 B2
(45) Date of Patent: Jul. 7, 2015

(54) GEOMETRIC OPTICAL POWER MEASUREMENT DEVICE

(71) Applicant: WaveTec Vision Systems, Inc., Aliso Viejo, CA (US)

(72) Inventors: Richard J. Michaels, Irvine, CA (US); Aric K. Plumley, Huntington Beach, CA (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 72 days.

(21) Appl. No.: 13/797,702

(22) Filed: Mar. 12, 2013

(65) Prior Publication Data

US 2014/0085604 A1    Mar. 27, 2014

Related U.S. Application Data

(60) Provisional application No. 61/706,630, filed on Sep. 27, 2012.

(51) Int. Cl.
*A61B 3/14* (2006.01)
*A61B 3/00* (2006.01)
(Continued)

(52) U.S. Cl.
CPC .............. *A61B 3/103* (2013.01); *A61B 3/0025* (2013.01)

(58) Field of Classification Search
CPC ............ A61B 3/14; A61B 3/12; A61B 3/103; A61B 3/113; A61B 3/1225; A61B 3/024; A61B 3/1015; A61B 3/032; A61B 3/135
USPC ......... 351/206, 200, 205, 209–210, 221–222, 351/246, 239, 211, 214, 223

See application file for complete search history.

(56) References Cited

U.S. PATENT DOCUMENTS

| 3,947,186 A | 3/1976 | Howland |
| 4,019,813 A | 4/1977 | Cornsweet et al. |
| 4,125,320 A | 11/1978 | Rassow |

(Continued)

FOREIGN PATENT DOCUMENTS

| AU | 2005234778 | 8/2011 |
| CA | 2515010 | 5/2013 |

(Continued)

OTHER PUBLICATIONS

International Search Report and Written Opinion, re PCT Application No. PCT/US 13/61729, mailed Apr. 22, 2014.

(Continued)

*Primary Examiner* — Dawayne A Pinkney
(74) *Attorney, Agent, or Firm* — Knobbe, Martens Olson & Bear, LLP (57) ABSTRACT

An ophthalmic optical power measurement device can include a light source configured to direct an input beam of light into the eye of a patient. The ophthalmic optical power measurement device can also include an aperture configured to receive an output beam that consists of light from the input beam that scatters from a location on the retina of the eye and exits through the pupil of the eye. The ophthalmic optical power measurement device can also include a detector configured to receive the output beam after it has passed through the aperture. A processor can be configured to determine the size of a spot created by the output beam on the detector, and to determine the optical power of the eye based upon the size of the spot.

22 Claims, 4 Drawing Sheets

(51) Int. Cl.
*A61B 3/10* (2006.01)
*A61B 3/103* (2006.01)

(56) References Cited

U.S. PATENT DOCUMENTS

| | | | |
|---|---|---|---|
| 4,172,662 A | 10/1979 | Vogel | |
| 4,173,398 A | 11/1979 | Okamoto et al. | |
| 4,293,198 A | 10/1981 | Kohayakawa et al. | |
| 4,353,625 A | 10/1982 | Nohda et al. | |
| 4,372,655 A | 2/1983 | Matsumura et al. | |
| 4,376,573 A | 3/1983 | Matsumura et al. | |
| 4,390,255 A | 6/1983 | Nohda et al. | |
| 4,421,391 A | 12/1983 | Matsumura et al. | |
| 4,459,027 A | 7/1984 | Kafri et al. | |
| 4,541,697 A | 9/1985 | Remijan | |
| 4,640,596 A | 2/1987 | Humphrey | |
| 4,650,301 A | 3/1987 | Humphrey | |
| 4,669,835 A | 6/1987 | Humphrey | |
| 4,692,003 A | 9/1987 | Adachi et al. | |
| 4,710,193 A | 12/1987 | Volk | |
| 4,721,379 A | 1/1988 | L'Esperance | |
| 4,730,917 A | 3/1988 | Krueger | |
| 4,911,711 A | 3/1990 | Telfair et al. | |
| 4,964,715 A | 10/1990 | Richards | |
| 4,984,883 A | 1/1991 | Winocur | |
| 4,995,716 A | 2/1991 | Warnicki et al. | |
| 5,080,477 A | 1/1992 | Adachi | |
| 5,144,478 A | 9/1992 | Toshimitsu | |
| 5,157,427 A | 10/1992 | Humphrey | |
| 5,164,750 A | 11/1992 | Adachi | |
| 5,202,708 A | 4/1993 | Sasaki et al. | |
| 5,206,672 A | 4/1993 | Rowe | |
| 5,208,619 A | 5/1993 | Campbell | |
| 5,223,863 A | 6/1993 | Heine | |
| 5,252,999 A | 10/1993 | Sukigara | |
| 5,258,791 A | 11/1993 | Penney et al. | |
| 5,270,749 A | 12/1993 | Okumura | |
| 5,282,852 A | 2/1994 | Capetan et al. | |
| 5,294,971 A | 3/1994 | Braunecker et al. | |
| 5,307,097 A | 4/1994 | Baker | |
| 5,329,322 A | 7/1994 | Yancey | |
| 5,374,193 A | 12/1994 | Trachtman | |
| 5,450,143 A | 9/1995 | Rowe et al. | |
| 5,455,645 A | 10/1995 | Berger et al. | |
| 5,493,109 A | 2/1996 | Wei et al. | |
| 5,576,780 A | 11/1996 | Yancey | |
| 5,777,719 A | 7/1998 | Williams et al. | |
| 5,796,463 A | 8/1998 | Bullimore | |
| 5,800,533 A | 9/1998 | Eggleston et al. | |
| 5,841,511 A | 11/1998 | D'Souza et al. | |
| 5,861,937 A | 1/1999 | Fujieda | |
| 5,909,268 A | 6/1999 | Isogai et al. | |
| 5,936,706 A | 8/1999 | Takagi | |
| 5,949,521 A | 9/1999 | Williams et al. | |
| 5,963,300 A | 10/1999 | Horwitz | |
| 5,968,094 A | 10/1999 | Werblin et al. | |
| 5,968,095 A | 10/1999 | Norrby | |
| 5,994,687 A | 11/1999 | Chanteloup et al. | |
| 6,002,484 A | 12/1999 | Rozema et al. | |
| 6,004,313 A | 12/1999 | Shimmick et al. | |
| 6,007,204 A | 12/1999 | Fahrenkrug et al. | |
| 6,042,232 A | 3/2000 | Luce et al. | |
| 6,043,885 A | 3/2000 | Mazuet et al. | |
| 6,050,687 A | 4/2000 | Bille et al. | |
| 6,086,204 A | 7/2000 | Magnante | |
| 6,095,651 A | 8/2000 | Williams et al. | |
| 6,096,077 A | 8/2000 | Callahan et al. | |
| 6,155,684 A | 12/2000 | Bille et al. | |
| 6,199,986 B1 | 3/2001 | Williams et al. | |
| 6,251,101 B1 | 6/2001 | Glockler | |
| 6,262,328 B1 | 7/2001 | Wicks et al. | |
| 6,264,328 B1 | 7/2001 | Williams et al. | |
| 6,270,221 B1 | 8/2001 | Liang et al. | |
| 6,271,915 B1 | 8/2001 | Frey et al. | |
| 6,275,718 B1 | 8/2001 | Lempert | |
| 6,299,311 B1 | 10/2001 | Williams et al. | |
| 6,299,618 B1 | 10/2001 | Sugiura | |
| 6,338,559 B1 | 1/2002 | Williams et al. | |
| 6,379,005 B1 | 4/2002 | Williams et al. | |
| 6,382,793 B1 | 5/2002 | Lai et al. | |
| 6,382,794 B1 | 5/2002 | Lai et al. | |
| 6,382,795 B1 | 5/2002 | Lai | |
| 6,394,605 B1 | 5/2002 | Campin et al. | |
| 6,409,345 B1 | 6/2002 | Molebny et al. | |
| 6,419,671 B1 | 7/2002 | Lemberg | |
| 6,439,720 B1 | 8/2002 | Graves et al. | |
| 6,460,997 B1 | 10/2002 | Frey et al. | |
| 6,497,483 B2 | 12/2002 | Frey et al. | |
| 6,508,812 B1 | 1/2003 | Williams et al. | |
| 6,511,180 B2 | 1/2003 | Guirao et al. | |
| 6,550,917 B1 | 4/2003 | Neal et al. | |
| 6,561,648 B2 | 5/2003 | Thomas | |
| 6,570,143 B1 | 5/2003 | Neil et al. | |
| 6,572,230 B2 | 6/2003 | Levine | |
| 6,575,572 B2 | 6/2003 | Lai et al. | |
| 6,578,963 B2 | 6/2003 | Pettit | |
| 6,585,723 B1 | 7/2003 | Sumiya | |
| 6,588,902 B2 | 7/2003 | Isogai | |
| 6,598,975 B2 | 7/2003 | Liang et al. | |
| 6,601,956 B1 | 8/2003 | Jean et al. | |
| 6,609,793 B2 | 8/2003 | Norrby et al. | |
| 6,609,794 B2 | 8/2003 | Levine | |
| 6,626,535 B2 | 9/2003 | Altmann | |
| 6,626,538 B1 | 9/2003 | Arrowsmith | |
| 6,634,751 B2 | 10/2003 | Turner et al. | |
| 6,637,884 B2 | 10/2003 | Martino | |
| 6,658,282 B1 | 12/2003 | Eagan et al. | |
| 6,679,606 B2 | 1/2004 | Campin et al. | |
| 6,685,319 B2 | 2/2004 | Watson et al. | |
| 6,702,806 B2 | 3/2004 | Gray et al. | |
| 6,705,729 B2 | 3/2004 | Piers et al. | |
| 6,724,464 B2 | 4/2004 | Yang et al. | |
| 6,736,509 B2 | 5/2004 | Martino et al. | |
| 6,736,510 B1 | 5/2004 | Van Heugten | |
| 6,739,721 B2 | 5/2004 | Altmann | |
| 6,761,454 B2 | 7/2004 | Lai et al. | |
| 6,781,681 B2 | 8/2004 | Horwitz | |
| 6,786,603 B2 | 9/2004 | Altmann | |
| 6,793,654 B2 | 9/2004 | Lemberg | |
| 6,819,413 B2 | 11/2004 | Neal et al. | |
| 6,827,444 B2 | 12/2004 | Williams et al. | |
| 6,836,374 B2 | 12/2004 | Esch et al. | |
| 6,905,641 B2 | 6/2005 | Platt et al. | |
| 6,908,196 B2 | 6/2005 | Herekar et al. | |
| 6,926,710 B2 | 8/2005 | Cox et al. | |
| 6,948,818 B2 | 9/2005 | Williams et al. | |
| 6,997,555 B2 | 2/2006 | Dick et al. | |
| 7,018,376 B2 | 3/2006 | Webb | |
| 7,034,949 B2 | 4/2006 | Horwitz | |
| 7,044,602 B2 | 5/2006 | Chernyak | |
| 7,044,604 B1 | 5/2006 | Arrowsmith | |
| 7,057,806 B2 | 6/2006 | Atkinson | |
| 7,066,928 B2 | 6/2006 | Dick et al. | |
| 7,068,439 B2 | 6/2006 | Esch et al. | |
| 7,070,276 B2 | 7/2006 | Koretz | |
| 7,077,522 B2 | 7/2006 | Williams | |
| 7,111,938 B2 | 9/2006 | Andino et al. | |
| 7,182,780 B2 | 2/2007 | Terwee et al. | |
| 7,237,898 B1 | 7/2007 | Hohla et al. | |
| 7,255,442 B2 | 8/2007 | Bucourt et al. | |
| 7,303,281 B2 | 12/2007 | Wakil et al. | |
| 7,336,371 B1 | 2/2008 | Haidner et al. | |
| 7,341,348 B2 | 3/2008 | Eagan | |
| 7,350,916 B2 | 4/2008 | Hong et al. | |
| 7,350,920 B2 | 4/2008 | Levine | |
| 7,357,509 B2 | 4/2008 | Williams et al. | |
| 7,374,286 B2 | 5/2008 | Fujieda et al. | |
| 7,377,641 B2 | 5/2008 | Piers et al. | |
| 7,380,942 B2 | 6/2008 | Molebny et al. | |
| 7,401,919 B2 | 7/2008 | Vogelsang et al. | |
| 7,406,263 B2 | 7/2008 | Graves et al. | |
| 7,416,305 B2 | 8/2008 | Williams et al. | |
| 7,425,067 B2 | 9/2008 | Warden et al. | |
| 7,441,901 B2 | 10/2008 | Liang | |

(56) References Cited

U.S. PATENT DOCUMENTS

| | | |
|---|---|---|
| 7,445,335 B2 | 11/2008 | Su et al. |
| 7,448,752 B2 | 11/2008 | Levine |
| 7,455,407 B2 | 11/2008 | Neal et al. |
| 7,461,938 B2 | 12/2008 | Lai |
| 7,467,869 B2 | 12/2008 | Kahlen |
| 7,475,989 B2 | 1/2009 | Campbell et al. |
| 7,476,248 B2 | 1/2009 | Harris et al. |
| 7,478,908 B2 | 1/2009 | Lai et al. |
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 | 9/2009 | Van Heugten |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,887,184 B2 | 2/2011 | Baer et al. |
| 7,988,291 B2 | 8/2011 | Ianchulev |
| 8,002,410 B2 | 8/2011 | Shea |
| 8,313,196 B2 | 11/2012 | Ianchulev |
| 8,333,474 B2 | 12/2012 | Michaels et al. |
| 8,394,083 B2 | 3/2013 | Van Heugten et al. |
| 8,475,439 B2 | 7/2013 | Van Heugten et al. |
| 8,480,659 B2 | 7/2013 | Frey et al. |
| 8,545,023 B2 | 10/2013 | Holladay et al. |
| 8,550,624 B2 | 10/2013 | Padrick et al. |
| 8,619,405 B2 | 12/2013 | Van Heugten |
| 8,632,185 B2 | 1/2014 | Ianchulev |
| 8,764,187 B2 | 7/2014 | Padrick et al. |
| 8,876,290 B2 | 11/2014 | Sarver et al. |
| 2001/0041884 A1 | 11/2001 | Frey et al. |
| 2002/0016629 A1 | 2/2002 | Sandstedt et al. |
| 2002/0082629 A1 | 6/2002 | Cox et al. |
| 2002/0097376 A1 | 7/2002 | Applegate et al. |
| 2002/0105617 A1 | 8/2002 | Norrby et al. |
| 2002/0107567 A1 | 8/2002 | Terwee et al. |
| 2002/0118349 A1 | 8/2002 | Yang et al. |
| 2002/0133228 A1 | 9/2002 | Sarver |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1 | 1/2003 | Levine |
| 2003/0007127 A1 | 1/2003 | Levine |
| 2003/0009156 A1 | 1/2003 | Levine |
| 2003/0025080 A1 | 2/2003 | Sting et al. |
| 2003/0053025 A1 | 3/2003 | Turner et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0054358 A1 | 3/2004 | Cox et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0007603 A1 | 1/2005 | Arieli |
| 2005/0068497 A1 | 3/2005 | Hanebuchi et al. |
| 2005/0105044 A1 | 5/2005 | Warden et al. |
| 2005/0110946 A1 | 5/2005 | Youssefi et al. |
| 2005/0110949 A1 | 5/2005 | Goldfain et al. |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2006/0007395 A1 | 1/2006 | Mayo et al. |
| 2006/0007397 A1 | 1/2006 | Lai |
| 2006/0084956 A1 | 4/2006 | Sumiya |
| 2006/0126018 A1 | 6/2006 | Liang |
| 2006/0126019 A1 | 6/2006 | Liang et al. |
| 2006/0135952 A1 | 6/2006 | Curatu et al. |
| 2006/0174281 A1 | 8/2006 | Park |
| 2006/0203196 A1 | 9/2006 | Van Heugten |
| 2006/0203198 A1 | 9/2006 | Liang |
| 2006/0232744 A1 | 10/2006 | Liang |
| 2006/0247659 A1 | 11/2006 | Moeller et al. |
| 2006/0279699 A1 | 12/2006 | Liang |
| 2007/0024808 A1 | 2/2007 | Campin et al. |
| 2007/0027442 A1 | 2/2007 | Campin et al. |
| 2007/0070292 A1 | 3/2007 | Liang |
| 2007/0070293 A1* | 3/2007 | Isogai .......................... 351/205 |
| 2007/0083261 A1 | 4/2007 | Colvard |
| 2007/0115432 A1 | 5/2007 | Thibos |
| 2007/0236702 A1 | 10/2007 | Neal et al. |
| 2007/0260157 A1 | 11/2007 | Norrby |
| 2008/0004610 A1 | 1/2008 | Miller et al. |
| 2008/0033546 A1 | 2/2008 | Liang |
| 2008/0084541 A1 | 4/2008 | Lai et al. |
| 2008/0088795 A1 | 4/2008 | Goldstein et al. |
| 2008/0159642 A1 | 7/2008 | Lyuboshenko |
| 2008/0231809 A1 | 9/2008 | Haigis |
| 2008/0278683 A1 | 11/2008 | Su et al. |
| 2008/0281304 A1 | 11/2008 | Campbell |
| 2008/0291396 A1 | 11/2008 | Baer et al. |
| 2009/0002628 A1 | 1/2009 | Williams et al. |
| 2009/0002631 A1 | 1/2009 | Campbell et al. |
| 2009/0009717 A1 | 1/2009 | Barrett et al. |
| 2009/0036980 A1 | 2/2009 | Norrby et al. |
| 2009/0048608 A1 | 2/2009 | Boukhny et al. |
| 2009/0096987 A1 | 4/2009 | Lai et al. |
| 2009/0103050 A1 | 4/2009 | Michaels |
| 2009/0109401 A1 | 4/2009 | Van Heugten |
| 2009/0164007 A1 | 6/2009 | Van Heugten |
| 2010/0030225 A1 | 2/2010 | Ianchulev |
| 2010/0036386 A1 | 2/2010 | Ianchulev |
| 2010/0042210 A1 | 2/2010 | Ianchulev |
| 2010/0152847 A1 | 6/2010 | Padrick et al. |
| 2011/0001960 A1 | 1/2011 | Van Heugten |
| 2011/0007270 A1 | 1/2011 | Sarver |
| 2011/0013141 A1 | 1/2011 | Holladay et al. |
| 2011/0015541 A1 | 1/2011 | Padrick |
| 2011/0242482 A1 | 10/2011 | Olsen |
| 2011/0267579 A1 | 11/2011 | Van Heugten |
| 2012/0147460 A1 | 6/2012 | Kubler |
| 2013/0021574 A1 | 1/2013 | Van Heugten |
| 2013/0070203 A1 | 3/2013 | Michaels |
| 2013/0131687 A1 | 5/2013 | Ianchulev |
| 2013/0335705 A1 | 12/2013 | Heugten |
| 2014/0111772 A1* | 4/2014 | Ikegami ....................... 351/211 |
| 2014/0132922 A1 | 5/2014 | Padrick |
| 2014/0132931 A1 | 5/2014 | Holladay |
| 2014/0249624 A1 | 9/2014 | Ianchulev |
| 2014/0313487 A1 | 10/2014 | Van Heugten |

FOREIGN PATENT DOCUMENTS

| | | |
|---|---|---|
| CN | 1942146 A | 4/2007 |
| CN | 102497833 A | 6/2011 |
| DE | 43 10 561 A1 | 9/1994 |
| DE | 19 85 7001 A1 | 6/2000 |
| EP | 0931504 A1 | 7/1999 |
| EP | 2444021 | 4/2012 |
| EP | 2453822 | 5/2012 |
| EP | 2453823 | 5/2012 |
| EP | 1596710 | 1/2013 |
| EP | 1 737 372 | 8/2014 |
| EP | 2 818 130 | 12/2014 |
| GB | 1 209 451 | 10/1970 |
| IL | 138282 | 7/2004 |
| JP | 11-24434 | 8/1989 |
| JP | 9-122075 | 5/1997 |
| JP | 10-272100 | 10/1998 |
| JP | 2000-139996 | 5/2000 |
| JP | 2000-197607 | 7/2000 |
| JP | 2001-507258 A | 6/2001 |

(56) References Cited

FOREIGN PATENT DOCUMENTS

| JP | 2001-314372 A | 11/2001 |
|---|---|---|
| JP | 2002-306418 A | 10/2002 |
| JP | 2003-509731 A | 3/2003 |
| JP | 2003-102689 A | 4/2003 |
| JP | 4972546 | 4/2012 |
| WO | WO 92/01417 | 2/1992 |
| WO | WO 96/22506 | 7/1996 |
| WO | WO 98/27863 | 7/1998 |
| WO | WO 00/33729 | 6/2000 |
| WO | WO 01/06914 | 2/2001 |
| WO | WO 01/21061 | 3/2001 |
| WO | WO 01/26591 | 4/2001 |
| WO | WO 01/58339 | 8/2001 |
| WO | WO 02/17775 | 3/2002 |
| WO | WO 03/002047 | 1/2003 |
| WO | WO 03/039356 | 5/2003 |
| WO | WO 03/050472 | 6/2003 |
| WO | WO 03/102498 | 12/2003 |
| WO | WO 2004/093663 | 11/2004 |
| WO | WO 2005/057252 | 6/2005 |
| WO | WO 2006/081031 | 8/2006 |
| WO | WO 2009/086059 | 7/2009 |
| WO | WO 2014/052479 | 4/2014 |

OTHER PUBLICATIONS

Combined International Search Report and Written Opinion of the International Searching Authority for International Application No. PCT/US05/13550; issued by the ISA/US; dated Nov. 15, 2005.
Restriction Requirement issued on Apr. 10, 2007 in U.S. Appl. No. 10/820,635, filed Apr. 8, 2004.
Non-Final Office Action issued on Jul. 11, 2007 in U.S. Appl. No. 10/820,635, filed Apr. 8, 2004.
Office Action Response filed on Jan. 11, 2008 U.S. Appl. No. 10/820,635, filed Apr. 8, 2004.
Final Office Action issued on Apr. 10, 2008 in U.S. Appl. No. 10/820,635, filed Apr. 8, 2004.
Office Action mailed May 30, 2008 in Chinese Patent Application 200580011803.6 filed Apr. 20, 2005.
Office Action mailed Jul. 25, 2008 in Chinese Patent Application No. 2004-80003472.7 filed Jan. 20, 2004.
Office Action mailed Nov. 5, 2008 in European Patent Application 04703599.3 filed Jan. 20, 2004.
International Search Report and Written Opinion for International Application No. PCT/US2008/080153 dated Jan. 23, 2009.
Request for Continued Examination and Amendment filed on May 11, 2009 in U.S. Appl. No. 10/820,635, filed Apr. 8, 2004.
Office Action mailed May 15, 2009 in Japanese Patent Application 2001-511810 filed Jul. 27, 1999.
Office Action mailed May 22, 2009 in Chinese Patent Application 200580011803.6 filed Apr. 20, 2005.
Notice of Allowance issued on May 26, 2009 in U.S. Appl. No. 10/820,635, filed on Apr. 8, 2004.
Office Action mailed Jun. 2, 2009, issued in U.S. Appl. No. 11/110,653, filed Apr. 20, 2005.
Office Action mailed Jul. 7, 2009, in U.S. Appl. No. 11/110,968, filed, Apr. 20, 2005.
Rejection Decision issued Aug. 14, 2009 in Chinese Patent Application No. 2004-80003472.7 filed Jan. 20, 2004.
Office Action issued on Sep. 10, 2010 in in U.S. Appl. No. 12/499,079, filed Jul. 7, 2009.
Preliminary Amendment filed Oct. 15, 2009 in U.S. Appl. No. 12/499,079, filed Jul. 7, 2009.
Office Action Response filed Dec. 1, 2009 in U.S. Appl. No. 11/110,653, filed Apr. 20, 2005.
Office action mailed Dec. 14, 2009 in European Patent Application 04703599.3 filed Jan. 20, 2004.
Office action mailed Dec. 18, 2009 in Japanese Patent Application 2006-502878 filed Jan. 20, 2004.
Office Action mailed Dec. 25, 2009 in Chinese Patent Application 200580011803.6 filed Apr. 20, 2005.

Office Action Response filed Jan. 7, 2010 in U.S. Appl. No. 11/110,968, filed, Apr. 20, 2005.
Office Action mailed Jan. 15, 2010, issued in European Application No. 05737636.0 filed Apr. 20, 2005.
Final Office Action mailed Feb. 1, 2010 in U.S. Appl. No. 11/110,653, filed Apr. 20, 2005.
Office Action mailed Feb. 9, 2010 in Japanese Patent Application 2001-511810 filed Jul. 27, 1999.
International Search Report and Written Opinion for International Application No. PCT/US2009/063651 mailed Mar. 9, 2010.
Office Action issued on Apr. 6, 2010 in corresponding Australian Patent Application No. 2005234778.
International Search Report and Written Opinion issued on Apr. 10, 2010 in connection with corresponding International Application No. PCT/US2008/080153, filed Oct. 16, 2008.
International Search Report and Written Opinion, issued Apr. 30, 2010 in related International Patent Application No. PCT/US08/81584, filed Oct. 29, 2008.
RCE and Amendment filed Jul. 30, 2010 in U.S. Appl. No. 11/110,653, filed Apr. 20, 2005.
Office Action mailed Aug. 20, 2010 in Japanese Application No. 2006-502878.
Restriction Requirement issued Aug. 26, 2010 in U.S. Appl. No. 12/206,974, filed Sep. 9, 2008.
Notice of Allowance issued Sep. 28, 2010 in U.S. Appl. No. 11/110,653, filed Apr. 20, 2005.
International Search Report and Written Opinion mailed Oct. 7, 2010 for International Application No. PCT/US2010/041229.
International Search Report and Written Opinion mailed Oct. 7, 2010 for International Application No. PCT/US2010/041242.
Final Office Action mailed Oct. 29, 2010 in U.S. Appl. No. 11/110,968, filed Apr. 20, 2005.
Office Action dated Nov. 2, 2010 in Japanese Application No. 2007-509613 (with English Translation).
Office Action mailed Feb. 28, 2011 in U.S. Appl. No. 12/581,061, filed Oct. 16, 2009.
Office Action mailed Feb. 20, 2009 in Chinese Patent Application No. 2004-80003472.7 filed Jan. 20, 2004.
Amendment filed on Mar. 9, 2011 in U.S. Appl. No. 12/499,079, filed on Jul. 7, 2009.
Notice of Allowance issued on Mar. 22, 2011 in U.S. Appl. No. 12/499,079, filed Jul. 7, 2009.
Office Action mailed in corresponding European Patent Application No. 04703 599.3 on Mar. 23, 2011.
Request for Continued Examination, Final Amendment and Summary of Interview, filed in corresponding U.S. Appl. No. 11/110,968 on Apr. 29, 2011.
English Translation of Office Action mailed May 13, 2011 in corresponding Japanese Application No. JP 2006-502878.
Preliminary Amendment filed Jul. 19, 2011 in corresponding U S. Appl. No. 13/021,594.
Final Office Action issued on Aug. 2, 2011 in corresponding U.S. Appl. No. 12/206,974.
Final Office Action issued on Sep. 6, 2011 in corresponding U.S. Appl. No. 12/581,061.
Notification of Reasons for Refusal mailed in corresponding Japanese Patent Application No. JP 2007-509613 on Oct. 11, 2011.
Office Action issued in corresponding European Patent Application No. 05737636 on Oct. 27, 2011.
Request for Continued Examination, Final Amendment and Summary of Interview, filed in corresponding U.S. Appl. No. 12/206,974 on Dec. 2, 2011.
Office Action issued on Jan. 17, 2012 in connection with Canadian Patent Application No. 2515010.
Office Action mailed on Jan. 25, 2012 in corresponding U.S Appl. No. 13/021,594, filed Feb. 4, 2011.
Supplemental Preliminary Amendment filed Feb. 1, 2012 in U.S. Appl. No. 13/363,287 filed Jan. 31, 2012.
Request for Continued Examination, Amendment and Terminal Disclaimer filed in connection with U.S. Appl. No. 12/581,061 on Mar. 5, 2012.
Decision to Grant issued on Mar. 13, 2012 in connection with Japanese Patent Application No. 2007-509613.

(56) References Cited

OTHER PUBLICATIONS

Notice of Allowance issued on Mar. 20, 2011 in connection with U.S. Appl. No. 12/581,061 on Mar. 5, 2012.
Request for Continued Examination and IDS filed in connection with U.S. Appl. No. 12/206,974 on Mar. 21, 2012
Notice of Allowance issued in corresponding U.S. Appl. No. 12/206,974, filed Dec. 22, 2011.
Extended Search Report issued on Mar. 26, 2012 in connection with European Patent Application No. 12151139.8.
Office Action issued on Mar. 26, 2012 in connection with European Application No. EP 05737636.
Decision of Rejection (and English Translation) issued on May 11, 2012 in corresponding Japanese Patent Application No. JP 2006-502878.
Office Action issued on May 16, 2012 in connection with U.S. Appl. No. 12/614,344, filed on Nov. 6, 2009.
Restriction Requirement issued on Jun. 8, 2012 in corresponding U.S. Appl. No. 12/835,665.
Office Action issued on Jun. 8, 2012 in connection with U.S. Appl. No. 12/740,753.
Notice of Allowance issued on Jul. 11, 2012 in corresponding U.S. Appl. No. 13/021,594.
Office Action Response filed Jul. 17, 2012 in connection with corresponding Canadian Patent Application No. CA2515010.
Notice of Allowance issued on Jul. 18, 2012 in corresponding U.S. Appl. No. 12/581,061.
Notice of Allowance issued on Aug. 6, 2012 in connection with corresponding U.S. Appl. No. 12/206,974, filed Sep. 9, 2008.
Non-Final Office Action issued on Aug. 24, 2012 in corresponding U.S. Appl. No. 12/835,668.
Preliminary Amendment filed on Sep. 14, 2012 in corresponding U.S. Appl. No. 13/750,080.
Notice of Allowance issued on Sep. 17, 2012 in corresponding Canadian Application No. CA 2,515,010.
Non-Final Office Action issued on Oct. 5, 2012 in U.S. Appl. No. 12/835,665.
Request for Continued Examination filed on Oct. 10, 2012 in corresponding U.S. Appl. No. 13/021,594.
Office Action issued on Oct. 25, 2012 in connection with corresponding U.S. Appl. No. 12/581,074.
Office Action issued on Oct. 26, 2012 in connection with corresponding U.S. Appl. No. 13/619,168.
Notice of Allowance issued on Oct. 30, 2012 in connection with corresponding U.S. Appl. No. 13/021,594.
Office Action issued on Nov. 5, 2012 in connection with corresponding U.S. Appl. No. 12/830,221.
Preliminary Amendment filed on Dec. 3, 2012 in corresponding U.S. Appl. No. 13/620,593.
Office Action issued on Dec. 17, 2012 in corresponding European Application No. 10800338.
European Search Report issued Dec. 21, 2012 in corresponding European Application No. 10800338.
Extended Search Report issued on Jan. 8, 2013 in connection with European Patent Application No. 10800335.
Office Action issued on Feb. 12, 2013 in connection with related Canadian Patent Application No. 2,561,388.
Final Office Action, issued on Feb. 19, 2013, in corresponding U.S. Appl. No. 12/835,668.
Office Action issued on Feb. 25, 2013, in corresponding U.S. Appl. No. 12/740,753.
Terminal Disclaimer and Interview Summary submitted on Feb. 27, 2013 in corresponding U.S. Appl. No. 13/619,168.
Office Action Response filed on Mar. 5, 2013 in corresponding U.S. Appl. No. 12/830,221.
Office Action issued on Apr. 4, 2013, in correspondng EP Application No. 12 151 139.8.
Office Action issued May 9, 2013 in connection with U.S. Appl. No. 12/581,074.
Notice of Allowance issued on May 16, 2013 in corresponding U.S. Appl. No. 13/619,787.

Notice of Allowance issued on Jun. 10, 2013 in corresponding U.S. Appl. No. 12/614,344. (Wavtc.024A).
Final Office Action on Jun. 20, 2013 in corresponding U.S. Appl. No. 12/830,221.
Request for Continued Examination and Response to Office Action filed Aug. 9, 2013 in corresponding U.S. Appl. No. 12/581074.
"IOL Power Calculations Piggyback Lens," http://doctor-hill.com/iol-main/piggyback.html, accessed on Feb. 24, 2010.
"Refractive Vergence Formula Piggyback IOL Intraocular Lens Calculations," http://doctor-hill.com/iol-mail/piggyback.html, accessed on Feb. 12, 2010.
Aramberri, "Intraocular lens power calculation after corneal infratructure surgery: Double-K Method," J Cataract Refract Surg 29:2063-2068 (Nov. 2003).
Argento et al., "Intraocular lens power calculation after refractive surgery," J Cataract Refract Surg 29:1346-1351 (Jul. 2003).
Binkhorst RD., "Intraocular lens power calculation", Int Ophthalmol Clin. 1979 Winter; 19(4):237-52. (Abstract).
Binkhorst, "Power of the Pre-Pupillary Pseudoshakos," B.J.O. 56:332-37 (1972).
Binkhorst, "The Optical Design of the Intraocular Lens Implants," Opthalmic Surg 6(3): 17-31 (1975).
Brandser R., "Accuracy of IOL calculation in cataract surgery", Acta Ophthalmol Scand. Apr. 1997.; 75(2):162-5 (Abstract).
Castro et al., "Tilt and decentration of Intraocular lenses in vivo from Purkinje and Scheimpflug imaging: Validation study," J. Cataract Refract. Surg. 2007; 33:418-429.
Chen et al., "Analysis of intraocular lens power calculation in post-radial keratotomy eyes," J Cataract Refract Surg 29:65-? (Jan. 2003).
Colenbrander, "Calculation of the Power of an Iris-Clip Lens for Distance Vision," Br. J. Ophthal. 57:735-40(1973).
Cordonnier, M., et al., "How accurate is the hand-held refractor Retinomax(R) in measuring cycloplegic refraction: a further evaluation", Strabismus. Sep. 1998;6(3):133-l42 (Abstract)
Cua et al., Intraocular lens calculations in patients with corneal scarring and irregular astigmatism, J Cataract Refract Surg 29:1352-1357 (Jul. 2003).
Dalens H, Marcellier JJ, Moussiere L., "Use of the SRK (Sanders-Retzlaff-Kraft) regression formula in the preoperative calculation of the power of crystalline implants" (Abstract).
Donoso R., et al., "Emmetropization at cataract surgery. Looking for the best IOL power calculation formula according to the eye length", Arch Soc Esp Oftalmol. Sep. 2003;78(8):477-80 (Abstract).
El-Baha SM, et al., "Intraoperatie biometry for intraocular lens (IOL) power calculation at silicone oil removal", Eur J Ophthalmol. Aug.-Sep. 2003;18(7):622-6. (Abstract).
El-Defrawy S., et al. "Evaluation of a hand-held autorefractor in children younger than 6" J Pediatr Ophthalmol Strabismus. 1998 ~ar-Apr;35(2):107-9 (Abstract).
Feiz, et al., "Intraocular Lens Power Calculation After Laser In Situ Keratomileusis for Myopia and Hyperopia—A Standard Approach," Cornea 20(8):792-797 (2001).
Feordorov et al. "Estimation of Optical Power of the Intraocular Lens," Vestn. Onamol 80(4):27-31 (1967).
Filip M., et al. "Post-operatory biometry and refraction results estimated and refraction surprises—clinical study", Oftalmologia. 2003;56(1):11-4 (Abstract).
Gernet, "IOL Calculation According to Gernet and the GOW 70 PC Programme," Abstract from Ophthalmologe 98:873-876 (2001).
Gimbel et al., "Accuracy and Predictability of Intraocular Lens Power Calculation After Laser In Situ Keratomileusis," J Cataract Refract Surg 27:571-576 (Apr. 2001).
Gimbel et al.,"Accuracy and Predictability of Intraocular Lens Power Calculation After photorefractive keratectomy," J Cataract Refract Surg 26:1147-1151 (Apr. 2000).
Gupta, et al., *"Design and use of an infrared Pupilometer for real-time pupil mapping in response to incremental illumination levels"* 2000 Optical Society of America, Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/

(56) References Cited

OTHER PUBLICATIONS

Refractive+Surgery+Feature/Aberrometer-aims-to-improve-refractive-cataract-ou/Article Standard/Article/detail/559856.

Hamilton et al., "Cataract Surgery in Patients with Prior Refractive Surgery", Current Opinion in Ophthalmology 14:44-53 (2003).

Happe W. et al., "Intraoperative Skiaskopie zur Bestimmung des Brechwerts einer zu implantierenden Intraokularlinse" [Intraoperative retinoscopy for determining the refractive value of an implantable intraocular lens] Klin. Monatsbl. Augenheilkd. vol. 210, No. 4, 1997, pp. 207-212.

Harvey et al., "Reproducability and accuracy of measurements with a hand held autorefractive in children," Journal of Opthalmology 81:941-948 (1997).

Hoffer KJ, et al., "A simple lens power calculation program for the HP-67 and HP-97 Calculators", JAm Intraocul Implant Soc. Oct. 1978; 4(4):197-9. (Abstract).

Hoffer, "Calculating Corneal Power After Refractive Surgery," Cataract & Refractive Surgery Today 4(4):23-25 (Apr. 2004).

Hoffer, "Mathematics and computers in intraocular lens calculation," Am Intra-Ocular Implant Soc. J. 1(1):4-5 (1975).

Holladay, et al., "A three-part system for refining intraocular lens power calculations," J. Cataract Refract Surg. 14:17-24 (Jan. 1988)

Holladay, Jack T., "Refractive Power Calculations for Intraocular Lenses in Phakic Eye," American Journal of Ophthalmology, Jul. 1993, pp. 63-66.

Holladay, JT et al., Refining Toric Soft Contact Lens Prescriptions. Clao J. 1984; 10:326-31.

Holladay, JT, et al. "Calculating the Surgically Induced Refractive Change Following Ocular Surgery", J. Cataract Refract. Surg. 1992; 18:429-43.

Hunt et al., "Evaluation of the measurement of refractive error by the PowerRefractor: a remote, continuous and binocular measurement system of oculomotor function,"Br. J. Opthalmol 87:1504-1508 (2003).

Inchulev, "Method for Intraoperative Refractive IOL Calculation," Poster Presentation at Ophthalmology Conference (Apr. 2004).

Ianchulev, et al. (Aug. 2005), "Intraoperative optical refractive biometry for intraocular lens power estimation without axial length and keratometry measurements," Journal of Cataract & Refractive Surgery, vol. 31, Issue 8, pp. 1530-1536, Abstract.

Isenberg et al., "Use of the HARK Autorefractor in Children," American Journal of Ophthalmology 131(4):438-441 (2001).

Iuorno JD, et al., "Clinical comparison of the Welch Allyn SureSight handheld auto refractor versus cycloplegic auto refraction and retinoscopic refraction", J AAPOS. Apr. 2004;8(2):123-7 (Abstract).

Ivanov MN, et al., "Formula for calculating the IOL focal power", Vestn Oftalmol. Jul.-Aug. 2003;119 (4):52-4 (Abstract).

Iwami S. et al., "Prediction of Postoperative Refraction Using Intraoperative Retinoscopy" Journal of Japanese Opthalmological Society, vol. 103, No. 7, 1999, pp. 551-555.

Koo, So, et al., "Comparison of IOL powers by corrected method in eyes after PRK and LASIK", Korean J Ophthalmol. Jun. 2002;16(1):26-31 (Abstract).

Kora et al., "Intraocular lens power calculation for lens exchange," J Cataract Surg 27:543-548 (Apr. 2001).

Liang, et al. "Comparison of the handheld Retinomax K-Plus 2 and on-table autokeratomerters in children with and without cycloplegia," J Cataract Refract Surg 30:670-674 (Mar. 2004).

Liang, et al. "Aberrations and Retinal Image Quality of the Normal Human Eye", J. Optical Society of America, vol. 14, No. 11, Nov. 1997.

Liang, et al. "Comparison of Measurements of Refractive Errors Between the Hand-held Retinomax and On-table Autorefractors in Cyclopleged and Noncyclopleged Children," American Journal of Ophthalmology 136(6): 1120-1128 (Dec. 2003).

Lipatov DV., "Assessment of the efficiency of different formulae applied to calculating the optic power of an intraocular lens in transscleral fixation", Vestn Oftalmol, Nov.-Dec. 2003;119(6):33-5 (Abstract).

Ma, et al., "Simple method for accurate alignment in toric phakic and aphakic intraocular lens implantation," J Cataract Refract Surg, Technique, Oct. 2008, vol. 34, pp. 1631-1636.

Mackool RJ., "The cataract extraction-refraction-implantation technique for IOL power calculation in difficult cases", J Cataract Refract Surg. Apr. 1998;24(4):434-5 (Abstract).

Masket, et al., "Atlas of Cataract Surgery," Book cover in 1 page. Front Matter in 11 pages (Table of Contents in 3 pages), Chapter 19 pages 147-158, Published by Martin Dunitz Ltd 1999, United Kingdom.

Methling D, Kalb G., "A New Program for Calculating Intraocular Lenses", Klin Monatsbl Augenheilkd. Oct. 1992;201 (4):247-53 (Abstract).

Moreno-Barriuso, et al., "Laser Ray Tracing Versus Hartmen-Shack Sensor for Measuring Optical Aberrations in the Human Eye", J. Optical Society of America, vol. 17, No. 6, Jun. 2000.

Nemeth et al., "Optical and ultrasound measurement of axial length and anterior chamber depth for intraocular lens power calculation," J Cataract Refract Surg 29:85-88 (Jan. 2003).

Olsen, "Theoretical approach to intraocular lens calculation using Gaussian optics," J Cataract Refract Surg 13:141-145 (Mar. 1987).

Olsen, "Theoretifal computer-assisted prediction versus SRK prediction of postoperative refraction after intraocular lens implantation," J Cataract Refract Surg 13:141-145 (Mar. 1987).

Orr et al., "Manifest Refraction Versus Autorefraction for Patients with Subfoveal Choroidal Neovascularization," Investigative Ophthalmology & Visual Science 42(2): 447-451 (Feb. 2001).

Oyo-Szerenyi et al., "Autorefraction/Autokeratometry and Subjective Refraction in Untreated and Photorefractive Keratectomy—Treated Eyes," Arch Ophthalmol. vol. 115 (Feb. 1997).

Photograph of Oculus Instrument, accessed at http://www.oculus.de/en/sites/popup_bild_gross.php?news=&id=1056 on Apr. 29, 2011.

Quiroga, et al., "*Fourier transform method for automatic processing of moire deflectograms*," Jun. 1999, Society of Photo-Optical Instrumentation Engineers, pp. 974-982.

Raj et al., "Clinical Evaluation of automated refractio in anterior chamber pseudophakia," British Journal of Ophthalmology 75:42-44 (1991).

Raj et al., "Objective autorefraction in posterior chamber pseudophakia," British Journal of Ophthalmology 74:731-733 (1990).

Raj PS, et al., "Comparative evaluation of the Allergan Humphrey 570 and Canon RK-I autorefractors: I. Objective autorefraction in normal subjects", Eye. 1992;6 (Pt 3):284-6 (Abstract).

Retzlaff J., "A new intraocular lens calculation formula", J Am Intraocul Implant Soc. Apr. 1980 6(2):148-52. (Abstract).

Rosales et al., "Phakometry and lens tilt and decentration using a custom-deveeloped Purkinje imaging apparatus: validation and measurements," Journal of the Optical Society of America, vol. 23, No. 3, Mar. 2006, pp. 509-520.

Rubin A., et al., "Refractive variation during autorefraction: multivariate distribution of refractive status", Optim Vis Sci. Jun. 1995;72(6):403-10 (Abstract).

Rubin A., et al., "Variation during autorefraction: influence of two different target types", Ophthalmic Physiol Opt. Jan. 1997;17(1):38-43 (Abstract).

Sanders et al., "Comparison of the SRK/T formula and other theoretical and regression formulas." J Cataract Refract Surg. 16:341-346 (May 1990).

Sanders et al., "Comparisons of the SRK198 formula and other second generation formulas," J Cataract Refract Surg 14;136-141 (Mar. 1988).

Senjo, et al., "Prediction of Postoperative Refraction Using Intraoperative Retinoscopy," Journal of Japanese Ophthalmological Society, 1999, vol. 103, No. 7, pp. 551-555, Abstract.

Siahmed K., et al., "Optic biometry in intraoacular lense calculation for cataract surgery. Comparison with usual methods", J Fr Ophtalol. Nov. 2001;24(9):922-6 (Abstract).

Siganos et al., "Autorefractometry after laser in situ keratomileusis," J Cataract Refract Surg 29:133-137 (Jan. 2003).

Supplemental Amendment filed Apr. 1, 2010 in U.S. Appl. No. 11/110,968, filed Apr. 20, 2005.

(56) References Cited

OTHER PUBLICATIONS

Supplementary European Search Report for Application No. 05737636.0, Dated Mar. 19, 2009.
Steele, G., et al., "Cycloplegic auto refraction results in pre-school children using the Nikon Retinomax Plus and the Welch Allyn SureSight", Optom Vis Sci. Aug. 2003;80(8):573-7 (Abstract).
Straub et al., "*Design of a compact Shack-Hartmann aberrometr for real-time measurement of aberrations in human eyes*," 2000 Optical Society of America, pp. 110-113.
Suto et al., "Adjusting intraocular lens power for sulcus fixation," J Cataract Refract Surg 29:1913-1917 (Oct. 2003).
Tabernero et al., "Instrument for measuring the misalignments of ocular surfaces," Optical Society of America, Oct. 30, 2006, vol. 14, No. 22.
Thall et al., "Linear Regression Software for Intraocular Lens Implant Power Calculation," American Journal of Ophthalmology 101:597-599 (May 1986).
Thijssen JM., "The emmetropic and the iseikonic implant lens: computer calculation of the' refractive power and its accuracy", Ophthalmologica 1975;171 (6):467-86 (Abstract).
Thompson et al., "A New Posterior Chamber Intraocular Lens Formula for Axial Myopes," Ophthalmology 91(5): 484-488 (May 1984).
Tromans et al., "Accuracy of intraocular lens power calculation in paediatric cataract surgery," Br J Ophthalmol 85:939-941 (2001).
Tseng, et al., "Calculating the optimal rotation of a misaligned toric intraocular lens," J Catactact Refract Surg, Laboratory Science, Oct. 2008, vol. 34, pp. 1767-1772.
Uozato et al., "Intraoperative Confirmation Device for IOL Centering," Folia Ophthalmologica Japonica, vol. 41, 1990, pp. 1325-1329.
Van Heugten, T., et al. "Validation of Novel Hartmann-Moire Wavefront Sensor with Large Dynamic Range", presented at Wavefront Congress, Feb. 17, 2008, available at http://www.wavefront-congress.org/info/listing_detail.asp?absID-12, last visited Feb. 28, 2008.
Villada Jr., et al., "Comparative evaluation of the Allergan Humphrey 570 and Canon RK-I autorefractors: II, Objective autorefraction in pseudophakes", Eye. 1992;6 (Pt 3):287-9 (Abstract).
Walline JJ, "Repeatability and validity of astigmatism measurements", J Refract Surg. Jan.-Feb. 1999; 15(1):23-31 (Abstract).
Wiechens, et al., "Bilateral Cataract after Phakic Posterior Chamber Top Hat-style Silicone Intraocular Lens," Journal of Refractive Surgery, Jul./Aug. 1997, vol. 13, No. 4, Cover and Table of Contents in 2 pages, pp. 392-397.
Wood IC., "A review of autorefractors", Eye. 1987;1 (Pt 4):529-35 (Abstract).
Yalvac IS, et al al., "Calculation of intraocular lens power with the SRK IIformula for axial high myopia" Eur J Ophthalmol. Oct.-Dec. 1996;6(4):375-8 (Abstract).
Zaldivar et al., "Intraocular lens power calculations in patients with extreme myopia" J Cataract Refract Surg 26:668-674 (May 2000).
Response to Restriction Requirement filed on May 3, 2007, in U.S. Appl. No. 10/820,635, filed Apr. 8, 2004.
Response to Office Action dated Nov. 2, 2010 filed in corresponding Japanese Application No. JP 2007-509613, on Apr. 4, 2011.
Response to Office Action mailed on Apr. 5, 2011 in corresponding Australian Patent Application No. 2005234778.
Response to Office Action filed corresponding U.S. Appl. No. 12/581,061 on Jun. 28, 2011.
Response to Office Action filed in corresponding Japanese Application No. JP 2007-509613, on Mar. 8, 2012.
Response to Office Action filed Dec. 10, 2012 in corresponding U.S. Appl. No. 12/740,753.
Notice of Allowance issued on Feb. 20, 2014 in corresponding U.S. Appl. No. 12/835,668.
Office Action issued on Apr. 11, 2014, in corresponding U.S. Appl. No. 12/581,074.
Canadian Office Action, re CA Application No. 2,561,388, dated May 12, 2014.
International Preliminary Report on Patentability, re PCT Application No. PCT/US13/61729, mailed Oct. 10, 2014.
Office Action issued on Oct. 17, 2014, in corresponding U.S. Appl. No. 13/797,365.
European Extended Search Report, re EP Application No. 14181278.4, dated Dec. 3, 2014.
International Search Report and Written Opinion, re PCT Application No. PCT/US14/59943, mailed Jan. 14, 2015.
Nanavaty, et al.: "Anterior capsule cover and axial movement of intraocular lens," Eye (2008) 22, 1015-1023.
Narvaez et al: "Accuracy of intraocular lens power predictin using the Hoffer Q. Holladay 1, Holladay 2, and SRK/T formulas," Journal of Cataract & Refractive Surgery,Dec. 2006.

\* cited by examiner

GEOMETRIC OPTICAL POWER MEASUREMENT DEVICE

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57. In particular, this application claims priority to U.S. Provisional Patent Application 61/706,630, filed Sep. 27, 2012, and entitled "GEOMETRIC OPTICAL POWER MEASUREMENT DEVICE," which is hereby incorporated by reference herein in its entirety.

BACKGROUND

1. Field

The field of the invention relates to instruments for performing optical power measurements of an eye.

2. Description of the Related Art

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple spherical and cylindrical errors that cause myopia, hyperopia, or regular astigmatism, to more complex refractive errors that can cause, for example, halos and starbursts in a person's vision.

Many interventions have been developed over the years to correct various ocular aberrations. These include sphero-cylindrical corrective optical elements, such as spectacles, contact lenses, and intraocular lenses (IOLs), or corneal refractive surgery, such as LASIK. The diagnosis and correction of ocular aberrations typically involves the use of an optical power measurement device to determine the optical power of the eye. Although many different types of objective optical power measurement devices have been created, simpler, less-expensive objective optical power measurement devices may be beneficial.

SUMMARY

An ophthalmic optical power measurement device is disclosed. In some embodiments, the ophthalmic optical power measurement device comprises: a light source configured to direct an input beam of light into the eye of a patient; an aperture configured to receive an output beam of light from the eye, the output beam of light comprising light from the input beam that scatters from a location on the retina of the eye and exits through the pupil of the eye; a detector configured to receive the output beam after it has passed through the aperture; and a processor configured to determine the size of a spot created by the output beam on the detector, and to determine the optical power of the eye based upon the size of the spot.

An ophthalmic optical power measurement method is disclosed. In some embodiments, the ophthalmic optical power measurement method comprises: directing an input beam of light into an eye such that the input beam scatters from a location on the retina, thus creating an output beam that exits through the pupil of the eye; determining the angular size of the output beam; and determining the optical power of the eye based on the angular size of the output beam.

BRIEF DESCRIPTION OF THE DRAWINGS

For purposes of summarizing the disclosure, certain aspects, advantages and features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein. Certain embodiments are illustrated in the accompanying drawings, which are for illustrative purposes only.

DETAILED DESCRIPTION

Figure 1:
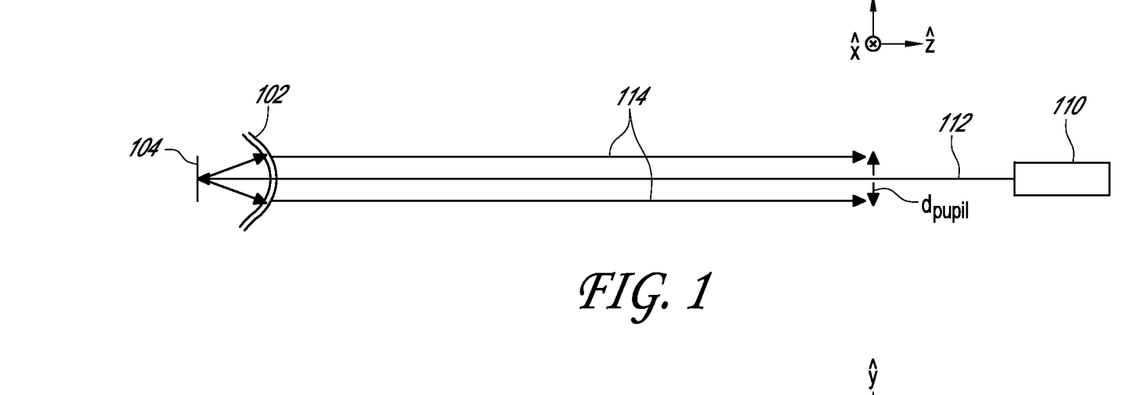
FIG. 1 is a schematic diagram of an input beam of light scattering from the retina of an emmetropic eye.

FIG. 1 is a schematic diagram of an input beam of light 112 scattering from the retina 104 of an emmetropic eye 102. The input beam of light 112 is emitted from a light source 110 along, for example, the visual axis or the optical axis of the emmetropic eye 102. The light source can be, for example, a laser or a super luminescent diode. The input beam of light 112 can be, for example, a collimated beam with a diameter of 1 mm or less. In some embodiments, the light source 110 outputs infrared light (e.g., 785 nm). The input beam of light 112 enters the emmetropic eye 102 at or near the corneal apex and propagates through the eye to the retina 104. Once the input beam of light 112 reaches the retina 104, it back scatters, thus creating an output beam of light 114. The size of the output beam 114 is limited by the pupil of the eye 102 through which it must pass to exit the eye. Since the eye 102 in FIG. 1 is emmetropic, the output beam 114 is substantially collimated. Thus, in the case of the emmetropic eye 102, the diameter of the output beam substantially corresponds to the diameter of the pupil, $d_{pupil}$. In the case of a hyperopic or a myopic eye, the output beam of light 114 will not be collimated but rather will be a diverging or converging beam of light.

Figure 2:
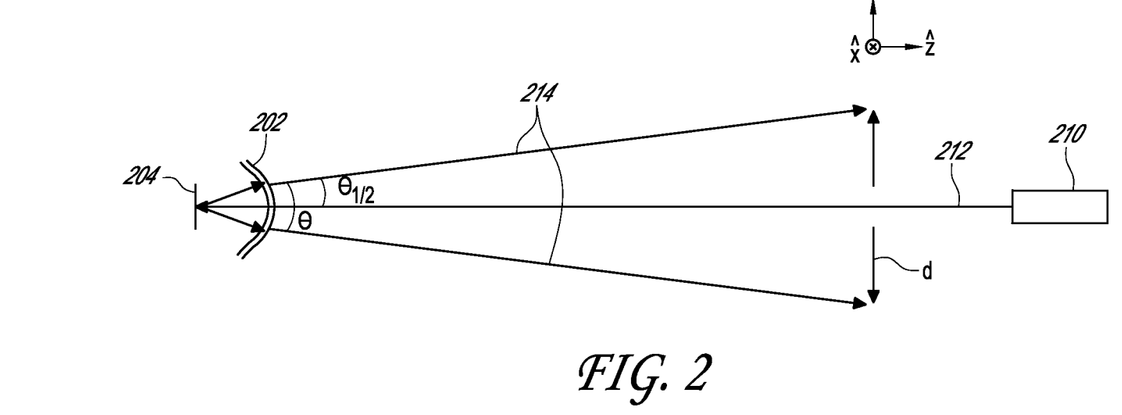
FIG. 2 is a schematic diagram of an input beam of light scattering from the retina of a hyperopic eye.

FIG. 2 is a schematic diagram of an input beam of light 212 scattering from the retina 204 of a hyperopic eye 202. The input beam of light 212 is emitted from a light source 210. The input beam of light 212 and the light source 210 can be, for example, similar to those described above with respect to FIG. 1. In FIG. 2, however, the output beam of light 214 is not collimated because the eye 202 is hyperopic. In other words, the eye 202 lacks sufficient optical power to collimate the output beam of light 214. Therefore, the output beam of light 214 is a diverging beam with a cone angle, θ, or a cone half angle, $θ_{1/2}$. Accordingly, the diameter, d, of the output beam 212 increases with increasing longitudinal distance, z, from the eye 202.

If the eye 202 is more severely hyperopic than illustrated in FIG. 2, then the cone angle will be greater. Similarly, if the eye 202 is less severely hyperopic than illustrated in FIG. 2, then the cone angle will be lesser. Although not illustrated, if the eye 202 were myopic, then the output beam of light 214 would be a converging beam as it exited the eye until reaching a focal point located outside of the eye. Beyond this point, it would become a diverging beam. Once again, the specific cone angle of the output beam 214 in the case of a myopic eye would vary as a function of the degree of myopia.

Since the cone angle of the output beam 214 varies as a function of the optical power of the eye 202, whether the eye be hyperopic (e.g., cone angle defined as θ>0), emmetropic (i.e., θ=0), or myopic (e.g., cone angle defined as θ<0), then a measurement of the cone angle can be used in order to determine the optical power of the eye 202. For example, the optical power (e.g., spherical and/or cylindrical) of the eye can be defined according to the following equation:

$$\phi = \frac{1}{EFL} \quad (1)$$

where EFL is the effective focal length of a lens at the corneal plane of an eye that achieves best focus on the retina from a collimated beam and is measured in, for example, meters. The EFL of the eye can, in turn, be defined according to the following equation:

$$EFL = \frac{d_{pupil}}{2\tan θ_{1/2}} \quad (2)$$

where $d_{pupil}$ is the diameter of the pupil of the eye and $θ_{1/2}$ is the cone half angle of the output beam of light 214. Thus, if the cone angle of the output beam of light and the diameter of the pupil of the eye can be determined, then the optical power of the eye can also be determined. In some embodiments, however, the measurement of the cone angle of the output beam is limited to a particular analysis zone of the pupil (e.g., a central ~4 mm portion of the pupil), as discussed herein. In such embodiments, the diameter of the analysis zone replaces the pupil diameter in Equation (2), and the optical power of the eye can be determined using the measured cone angle without determining the diameter of the pupil of the eye.

Figure 3:
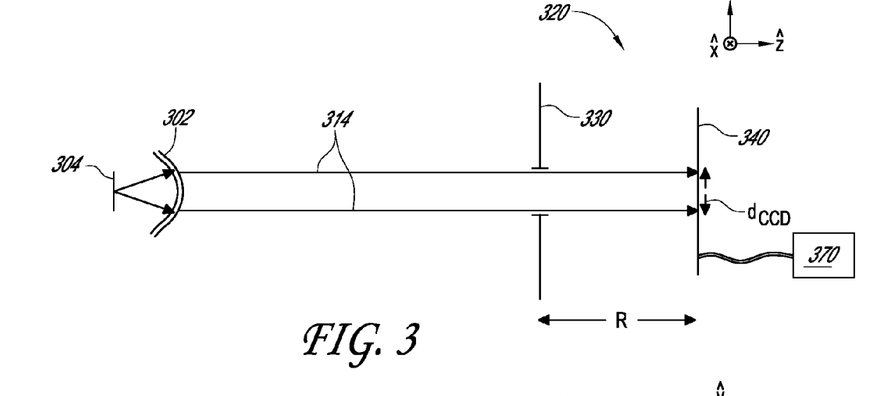
FIG. 3 is a schematic diagram of an optical power measurement device for determining the cone angle of an output beam of light from an eye.

FIG. 3 is a schematic diagram of an optical power measurement device 320 for determining the cone angle of an output beam of light 314 from an eye 302. Although not illustrated in FIG. 3, the optical power measurement device 320 can include a light source (e.g., similar to light source 110) to direct an input beam of light (e.g., similar to input beam 112) into the eye 302 (e.g., via a beamsplitter). The input beam of light back scatters from the retina 304, thus forming the output beam of light 314. The optical power measurement device 320 can also include a computing device 370 that can be used, for example, to analyze detector images and/or control the aperture 330, as discussed herein.

The optical power measurement device 320 also includes an aperture 330 and a detector 340. The aperture 330 can be, for example, circular in shape and can have a fixed or dynamically variable diameter, as discussed further herein. The detector 340 can be, for example, a CCD, CMOS, array of sensor elements, film, or a scanning detector. Alternatively, the detector 340 can be the combination of a diffuse surface that is imaged by a camera (not shown).

An optical axis for the optical power measurement device 320 can be defined, for example, as the axis that is normal to the surface of the detector 340 and passes through the center of the aperture 330. In some embodiments, the optical power measurement device 320 also includes an alignment system (not shown) for aligning the optical measurement device 320 to the eye 302. For example, in some embodiments, an alignment system can be used to position the optical power measurement device 320 (e.g., in the x and y directions) such that its optical axis is coincident with the optical axis or visual axis of the eye 302. In addition, the alignment system can be used to position the optical power measurement device 320 (e.g., in the z direction) at a known distance from the eye 302, as discussed herein. An example of such an alignment system is disclosed in U.S. Pat. No. 8,333,474, filed Sep. 9, 2008, and entitled "OPTICAL INSTRUMENT ALIGNMENT SYSTEM," the entire contents of which are incorporated by reference herein.

When the optical power measurement device 320 is adequately optically aligned to the eye 302, the output beam of light 314 passes through the aperture 330 and is incident upon the detector 340, thus forming a spot on the detector 340. The aperture 330 can be sized, for example, such that various output beams 314 with a desired range of cone angles (which, in turn, correspond to a range of ocular optical powers) do not underfill the aperture 330 when the optical power measurement device 320 is positioned at a desired distance from the eye 302 (e.g., the aperture 330, rather than the pupil of the eye, can be the limiting aperture of the output beam). In other words, in some embodiments, it is desirable that the aperture 330 be sized such that the diameter of the output beam of light 314 is at least as large as the aperture 330 at the point where the output beam 314 enters the aperture. The width of the output beam 314 can be defined using various measurements, such as, for example, the full width at half maximum (FWHM) of the beam.

The cone angle, $θ_{1/2}$, of the output beam of light 314 can be measured by the optical power measurement device 320 by, for example, determining the size of the spot formed by the output beam 314 on the detector 340, and then comparing the spot size to the size of the aperture 330. The size of the spot on the detector 340 can be determined using various measurements, such as, for example, the full width at half maximum of the spot. The comparison between the spot size and the aperture diameter can be done, for example, according to the following equation:

$$\tan θ_{1/2} = \frac{d_{CCD} - d_{aperture}}{2R} \quad (3)$$

where $d_{CCD}$ is the size (e.g., diameter) of the spot formed by the output beam on the detector 340, $d_{aperture}$ is the size (e.g., diameter) of the aperture 330, and R is the known distance between the aperture 330 and the detector 340 along the optical axis.

Figure 4:
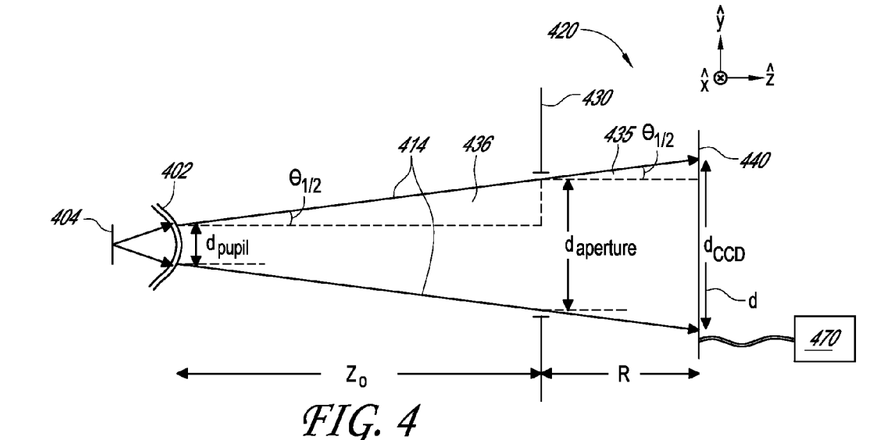
FIG. 4 is a schematic diagram of an optical power measurement device for determining the cone angle of an output beam of light from a hyperopic eye.

Equation (3) can be derived from, for example, one of the right triangles 435 formed by the intersection of the edge of the output beam 414, the detector 440, and a line perpendicular to the detector 440 at the perimeter of the aperture 430. As indicated in FIG. 4, one of the angles of such a right triangle 435 is the cone half angle, $θ_{1/2}$, of the output beam 414. The length of the leg of the triangle 435 opposite $\theta_{1/2}$ is half the difference between the diameter of the spot on the detector 440 and the diameter of the aperture 430. The length of the remaining leg of the triangle 435 is given by R, the distance between the aperture 430 and the detector 440. Accordingly, Equation 3 follows by application of the geometric definition of the tangent function to the right triangle 435. Other methods and/or equations can also be used, however, to compare the spot size of the output beam 314 on the detector 340 to the size of the aperture 330 in order to give an indication of the cone angle of the output beam.

In the case of an emmetropic eye 302, as is illustrated in FIG. 3, the output beam of light 314 is substantially collimated. Therefore, the size of the spot formed on the detector 340 by the output beam 314 is substantially the same (ignoring diffraction) as the size of the aperture 330. Accordingly, per Equation (3), the cone half angle of the output beam 314 equals zero, as illustrated in the following equation:

$$\tan\theta_{1/2} = \frac{d_{CCD} - d_{aperture}}{2R} = 0 \quad (4)$$

FIG. 4 is a schematic diagram of an optical power measurement device 420 for determining the cone angle of an output beam of light 414 from a hyperopic eye 402. The optical power measurement device 420 includes an aperture 430, a detector 440, and a computing device 470. The optical power measurement device 420 can be similar, for example, to the one (i.e., 320) discussed herein with respect to FIG. 3. However, the optical power measurement device 430 in FIG. 4 has a larger aperture 430 in order to accommodate the diverging output beam 414 from the hyperopic eye 402. Since the output beam 414 is a diverging beam, it forms a spot on the detector 440 that is larger than the aperture 430. Application of Equation (3) to the optical power measurement device 420 and the hyperopic eye 402 of FIG. 4 gives the following result:

$$\tan\theta_{1/2} = \frac{d_{CCD} - d_{aperture}}{2R} > 0 \quad (5)$$

Alternatively, if the optical power measurement device were used to measure the optical power of a myopic eye by analyzing a converging output beam, then the spot on the detector would be smaller than the aperture, and application of Equation (3) would result in a cone half angle measurement that is less than zero. Note that, in some embodiments, the optical power measurement device 420 is designed to measure the converging beam from a myopic eye at a location nearer to the eye than the focal point of the converging beam. This could constrain the dynamic range of the optical power measurement device 420 and/or the working distance between the optical power measurement device 420 and the eye. For example, a −4.0 D eye would focus the output beam 414 at a point 250 mm from the corneal apex. Thus, the optical power measurement device 420 could be located nearer to the eye (e.g., one prototype is designed to be positioned 130 mm from the corneal aperture) in order to measure the cone angle of the output beam before the focal point of the beam. Alternatively, in some embodiments, the optical power measurement device 420 may include optics for relaying the wavefront of the converging beam as it exits the pupil to, for example, the aperture 430 so as to reduce constraints on the dynamic range and/or working distance of the device when measuring myopic eyes.

In some embodiments, the size of the aperture 430 is adjustable to accommodate a variety of output beams 414 from eyes with different amounts of optical power. For example, the aperture 430 can be stopped down in the case of a converging output beam from a myopic eye, while the size of the aperture 430 can be increased in the case of a diverging output beam from a hyperopic eye. In some embodiments, the optical power measurement device has a dynamic range of at least about −5.0 Diopters to about +20.0 Diopters. In addition, in some embodiments, the size of the aperture 430 is dynamically adjusted in order to pass only light that exits from a desired portion, or analysis zone, of the pupil of the eye 402. For example, it may be desirable to perform measurements using substantially only light that exits a central optical zone of the pupil. In some embodiments, the analysis zone is the central optical zone of the pupil that is approximately 4 mm in diameter. By limiting the output beam 414 to light that exits from the central optical zone of the pupil, it may be possible to increase the consistency of optical power measurements made using the device 420 since the measurements will be less dependent upon pupil size, which can vary depending upon ambient lighting conditions, and optical aberrations that may affect light that passes through the outer periphery of the pupil.

In some embodiments, the size of the aperture 430 could be made to correspond to a defined analysis zone on the eye and the size of the aperture 430 could be controlled (e.g., using an iterative process and/or a feedback loop, or any other suitable method) with the measured divergence/convergence to ensure the aperture 430 is the correct size. For example, in some cases, the measured cone angle of the output beam, and the corresponding measured refractive power of the eye, may be dependent upon spherical aberration that is induced by the outer optical periphery of the eye being measured. Accordingly, the measured cone angle/refractive power may change somewhat as the size of the aperture 430 is dynamically adjusted to include or exclude portions of the output beam that pass through outer portions of the pupil of the eye. Calibration data, such as a calibration curve, can be determined a priori, using calibrated model eyes (e.g., of one or more optical powers), calibration lenses, etc., to define the relationship between spherical aberration and the measured cone angle/refractive power. Measurements of the cone angle/refractive power can be taken at a plurality of diameter settings for the aperture 430. The calibration data can then be used to determine which of the diameter settings for the aperture 430 corresponds to the desired analysis zone of the pupil (e.g., by fitting the measured values to a calibration curve). For example, a first measurement could be taken at an aperture size, such as 4 mm. Using the calibration data, it may be determined that the first measurement may correspond to an analysis zone of, for example, 6 mm at the pupil. The aperture size can then be adjusted (e.g., based on the calibration data) and a second measurement taken. This process can be continued until it is determined that the aperture size corresponds to the desired analysis zone of the pupil.

In some embodiments, in the case of a hyperopic eye that produces a diverging output beam, the size of the aperture 430 could be defined or adjusted by using the following relationship:

D=(pupil diameter)+(distance from the aperture to corneal apex)*tan $\theta_{1/2}$ In the case of a myopic eye that produces a converging beam, the diameter of the aperture could be defined or adjusted by using the following relationship:

D=(pupil diameter)−(distance from the aperture to corneal apex)*tan θ$_{1/2}$ With this control scheme, it follows that the larger the divergence, or more hyperopic the measurement, the larger the aperture 430 would become. These control schemes are but examples. Other control schemes can also be used.

Figure 5:
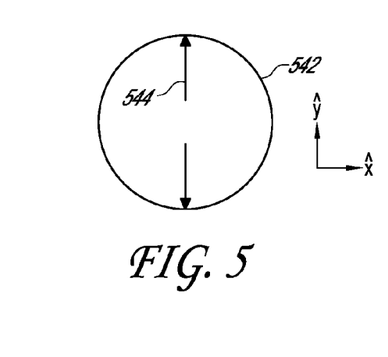
FIG. 5 is a schematic diagram of a spot formed on a detector by an output beam from an eye that does not exhibit substantial astigmatic power.

FIG. 5 is a schematic diagram of a spot 542 formed on a detector (e.g., 440) by an output beam (e.g., 414) from an eye that does not exhibit substantial astigmatic power. As illustrated, the spot 542 is substantially circular, indicating that the primary optical aberration of the eye from which the output beam was measured is rotationally-symmetric defocus error. (The eye could also have zero defocus error, depending upon the cone angle of the output beam.) The amount of defocus error can be characterized by measuring the diameter 544 of the spot 542 along any axis in the x-y plane of the detector. For example, the diameter 544 of the spot 542 can be determined and then compared to the diameter of the aperture (e.g., 430) of the optical power measurement device (e.g., 420) using Equation (3). In this way, the cone angle of the output beam (e.g., 414) can be determined. This value can then be used to calculate the effective focal length and/or spherical optical power of the eye, as discussed herein.

Figure 6:
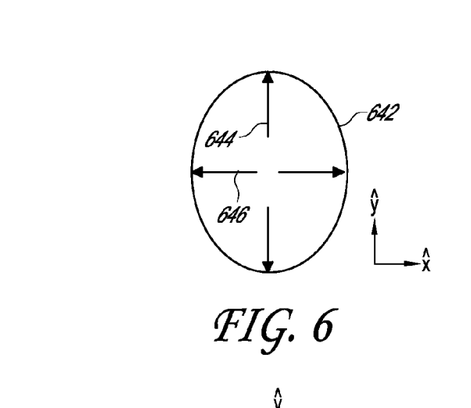
FIG. 6 is a schematic diagram of a spot formed on a detector by an output beam from an eye that exhibits astigmatic power.

FIG. 6 is a schematic diagram of a spot 642 formed on a detector (e.g., 440) by an output beam (e.g., 414) from an eye that exhibits astigmatic power. As illustrated, the spot 642 is ellipse-shaped, indicating that the optical power of the eye from which the output beam was measured is not entirely rotationally-symmetric. Specifically, the ellipse-shaped spot 642 indicates that the eye has a different degree of optical power in each of two orthogonal meridians (i.e., cylindrical or astigmatic power). The optical power in each of the two meridians can be measured by determining the respective sizes of the spot 642 in the direction of the major axis 644 and in the direction of the minor axis 646. Each of these measurements can be compared to the diameter of the aperture (e.g., 430), by application of Equation (3), in order to measure the cone angle of the output beam (e.g., 414) along the axes of the astigmatic power of the eye. As discussed herein, these values can then be used to calculate the effective focal lengths of the eye in each of the orthogonal meridians and/or the spherical and astigmatic optical power of the eye. In addition, the angular orientation of the major axis 644 or the minor axis 646 on the detector (i.e., the angle between either of the axes and a reference direction) can be determined in order to identify the axis of the patient's astigmatism. For example, in FIG. 6, the major axis 644 is parallel to the y-axis, while the minor axis 646 is parallel to the x-axis. However, this need not necessarily be the case, as the ellipse can have any orientation in the x-y plane of the detector, and its orientation will be indicative of the axis of the cylindrical power of the eye. As already discussed, the size of the ellipse in the directions of the major and minor axes will be indicative of the magnitude of the cylindrical power of the eye.

While FIGS. 5 and 6 illustrate how spherical and cylindrical power of an eye can be measured using the optical power measurement devices described herein, higher-order aberrations can also be measured in some embodiments. This can be done, for example, by introducing a Hartmann plate in the aperture (e.g., 430) of the device and performing additional analyses of the resulting spot formed by the passage of the output beam (e.g., 414) through the Hartmann plate and onto the detector (e.g., 440).

Once the angular size(s) (e.g., cone half angle(s)) of the output beam (e.g., 414) is/are determined, the effective focal length(s) and/or optical power(s) of the eye can likewise be determined. Some embodiments may not involve an additional measurement of the diameter of the pupil because the cone angle measurement may be limited to a selected analysis zone of the pupil (e.g., by making the aperture of the measurement device the limiting aperture of the output beam). However, in some embodiments, the pupil diameter is also used to determine the effective focal length(s) and/or optical power(s) of the eye, as indicated in, for example, Equations (1) and (2).

There are various ways to determine the diameter of the pupil of the eye. For example, in some embodiments, the diameter of the pupil is determined in a manner similar to that which was used to measure the cone half angle in Equation (3), as discussed with reference to FIG. 4. A similar equation can be written using a similar right triangle 436 that is formed by the intersection of the edge of the output beam 414, the plane of the aperture 430, and a line perpendicular to the plane of the aperture 430 at the perimeter of the pupil of the eye 402. Specifically, the equation can be written as follows:

$$\tan\theta_{1/2} = \frac{d_{aperture} - d_{pupil}}{2z} \Rightarrow d_{pupil} = d_{aperture} - 2z\tan\theta_{1/2} \tag{6}$$

where $d_{aperture}$ is the size (e.g., diameter) of the aperture 430, $d_{pupil}$ is the size (e.g., diameter) of the pupil of the eye 402, $\theta_{1/2}$ is the cone half angle output beam 414, which is measured using the optical power measurement device 420, and $z_0$ is a known distance between the eye 402 (e.g., the pupil plane) and the plane of the aperture 430 along the optical axis. Equation (6) follows from the application of the geometric definition of the tangent function to the right triangle 436. As discussed herein, the distance, $z_0$, or some other correlated distance (e.g., the distance $z_0'$ between the corneal apex and the optical power measurement device 420) can be determined using, for example, an alignment system to position the optical power measurement device 420 at a known distance from the eye 402 along the optical or visual axis of the eye. Alternatively, and/or additionally, the distance, $z_0$, or some other correlated distance can be determined using rangefinding, triangulation, distance-measuring interferometry, or some other measurement.

As shown herein, once the cone half angle of the output beam is determined using, for example, Equation (3), and the pupil diameter is determined using, for example, Equation (6), the effective focal length and/or the optical power of the eye 402 can be determined using Equations (1) and (2). (Incidentally, Equation (2) can be derived on the basis of yet another right triangle (inside of the eye) that is similar to right triangles 435 and 436.) While FIG. 4 schematically illustrates a method in which pupil diameter is determined, in part, by positioning the optical power measurement device 420 at a known distance, $z_0$, from the eye 402, other methods are also possible.

Figure 7:
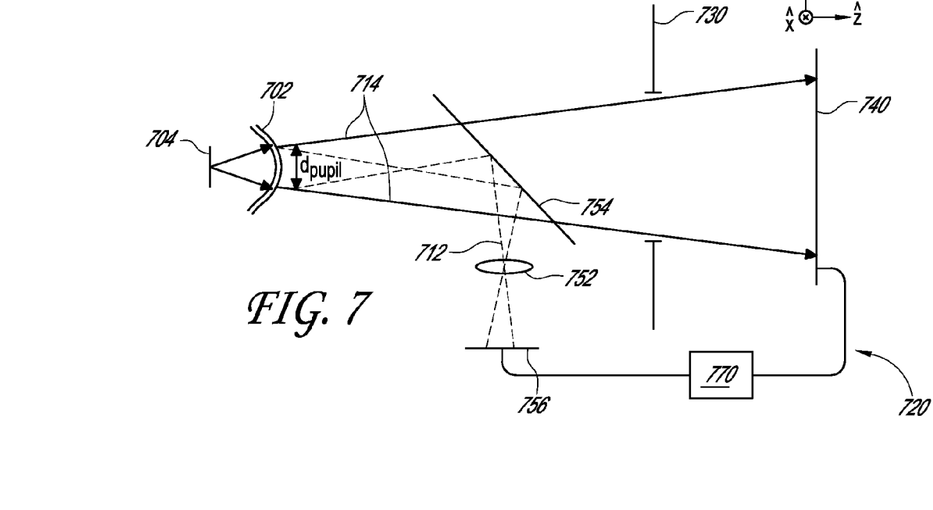
FIG. 7 is a schematic diagram of an optical power measurement device that includes a pupil imaging lens for optically determining the diameter of the pupil of an eye.

FIG. 7 is a schematic diagram of an optical power measurement device 720 that includes a pupil imaging lens 752 for optically determining the diameter of the pupil of an eye 702. The optical power measurement device 720 includes an aperture 730 and a detector 740, which may be similar to those described elsewhere herein. The optical power measurement device 720 can also include a computing device 770 that can be used, for example, to analyze detector images and/or control the aperture 730, as discussed herein. In addition, the optical power measurement device 720 in FIG. 7 includes a pupil imaging lens 752. Light from the pupil is directed to the pupil imaging lens 752 by, for example, a beam splitter 754. The pupil imaging lens 752 forms an image of the pupil of the eye 702 on a pupil imaging detector 756. In other words, the pupil imaging detector 756 and the pupil of the eye 702 can be located at the respective conjugate planes of the pupil imaging lens 752. The pupil imaging lens 752 can be a fixed-focus lens, or a variable-focus lens. It can include one or more optical elements.

The diameter, $d_{pupil}$, of the pupil can be determined by, for example, identifying the size of the pupil on the pupil imaging detector 756. The size of the pupil on the detector 756 can then be related to the actual size of the pupil based on the magnification of the pupil imaging lens 752. As discussed herein, once the pupil diameter is determined, it can be used in conjunction with the measured value of the angular size of the output beam 714 in order to determine the effective focal length and/or the optical power of the eye 702 using Equations (1) and (2).

Figure 8:
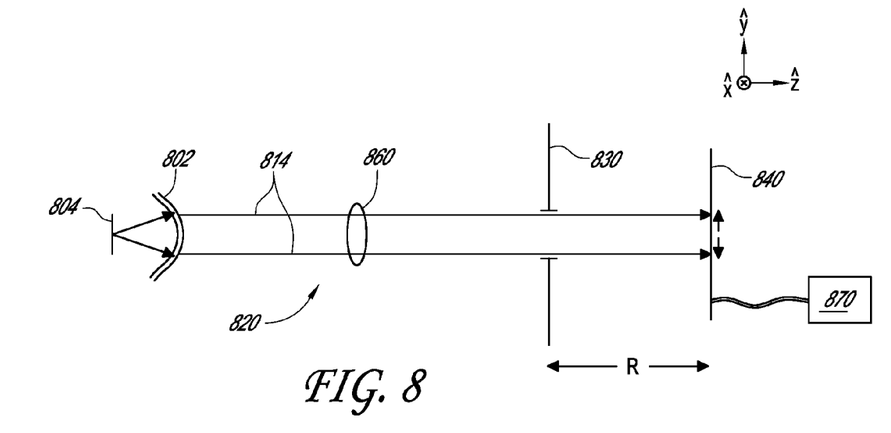
FIG. 8 is a schematic diagram of an optical power measurement device that includes a relay lens for relaying the output beam to the aperture.

FIG. 8 is a schematic diagram of an optical power measurement device 820 that includes a relay lens 860 for relaying the output beam 814 to the aperture 830. The optical power measurement device 820 also includes a detector 840 and a computing device similar to those described elsewhere herein. As discussed with respect to FIG. 4, the size of the aperture (e.g., 430) is adjustable and movable in some embodiments of the optical power measurement device. This can allow for an increase in the dynamic range of optical powers that can be measured. In addition, an adjustable aperture (e.g., 430) can be used to gather light from a consistent central optical zone of the pupil in order to increase reliability of the optical power measurements. The optical power measurement device 820 of FIG. 8, however, includes a relay lens 860 (e.g., with adjustable magnification) that may, in some embodiments, obviate a need for an adjustable aperture. Thus, in some embodiments, the relay lens 860 in the optical power measurement device 820 is accompanied by a fixed aperture 830.

The relay lens 860 can be a fixed-focus lens or a variable-focus lens. The relay lens 860 can include one or more optical elements. In operation, the relay lens 860 can be focused, for example, on the pupil of the eye 802, and can form an image of the pupil at the plane of the aperture 830. In this way, the relay lens 860 relays the output beam 814, as it exists at the pupil of the eye 802, to the aperture 830. The relay lens 860 therefore may allow the optical power measurement device 820 to measure a variety of output beams 814 with differing angular sizes without necessarily requiring that the aperture 830 be re-sized to accommodate the different output beams. In addition, the size of the aperture 830 can be set, depending upon the magnification of the relay lens 860, to correspond to a desired optical zone of the pupil (e.g., a central 4 mm zone of the pupil). For example, if the relay lens 860 gives 1:1 magnification, then if the aperture 830 has a diameter of 4 mm, it will transmit light only from a 4 mm optical zone of the pupil. As disclosed herein, by maintaining a consistent analysis zone of the pupil, the consistency and accuracy of optical power measurements can be improved.

Figure 9:
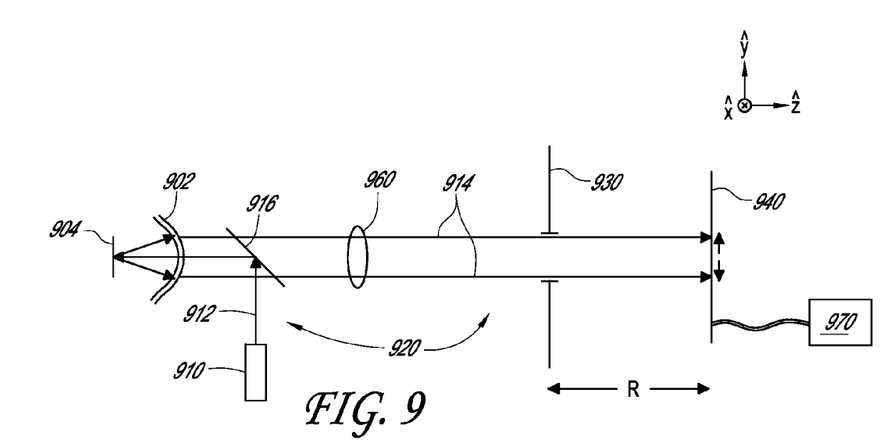
FIG. 9 is a schematic diagram of an optical power measurement device that includes an aperture, a detector, a light source, and a computing device.

FIG. 9 is a schematic diagram of an optical power measurement device 920 that includes an aperture 930, a detector 940, a light source 910, and a computing device 970. As illustrated in FIG. 9, the optical power measurement device 920 also includes a beam splitter 916 for directing the input beam 912 from the light source 910 into the eye 902. A relay lens 960 is also illustrated. While not shown, the optical power measurement device 920 may also include pupil imaging optics. Each of these elements can be similar to any of the corresponding elements described elsewhere herein. For example, the light source 910 can be an infrared laser or super luminescent diode. The aperture 930 can be fixed or variable.

As illustrated, the optical power measurement device 920 can include a computing device 970 having, for example, a processor and memory. The computing device 970 can include one or more modules (e.g., software and/or hardware) for determining the angular size of the output beam 914 and for determining the optical power of the phakic, aphakic, or pseudophakic eye 902 based on the angular size of the output beam. The computing device 970 can determine the angular size of the output beam 914 by using one or more modules to determine the size of the spot formed by the output beam 914 on the detector 940, and to compare that size to the size of the aperture 930. The computing device 970 can be designed, for example, to measure the size of the spot on the detector 940 along one or more axes. In addition, the computing device 970 can determine the size of the pupil of the eye 902, for example, based upon the size of the pupil on a pupil imaging detector or based upon the optical power measurement device 920 being located a known distance from the eye 902. The computing device 970 can control the size of the aperture 830 to measure a desired portion of the output beam 814 from the eye 802. In addition, the computing device 970 can calculate a suitable spherical and/or cylindrical power for an intraocular lens (IOL) to be inserted into the eye 902, as discussed, for example, in U.S. Pat. No. 7,556,378, filed Apr. 8, 2004, and entitled "INTRAOPERATIVE ESTIMATION OF INTRAOCULAR LENS POWER," and U.S. Patent Publication 2011/0015541, filed Jul. 13, 2010, and entitled "DETERMINATION OF THE EFFECTIVE LENS POSITION OF AN INTRAOCULAR LENS USING APHAKIC REFRACTIVE POWER," the entire contents of both of which are incorporated by reference herein.

In some embodiments, the optical power measurement device 920 includes an alignment system for precisely positioning the device transversely and longitudinally with respect to the eye 902. The alignment system can be, for example, similar to the one disclosed in U.S. Pat. No. 8,333,474, which was previously incorporated by reference herein.

In some embodiments, the optical power measurement device 920 is a desktop device or a handheld device. Alternatively, the optical power measurement device 920 can be designed to be integrated with a surgical microscope that is suitable for performing cataract surgery. For example, the optical power measurement device 920 can be integrated with a surgical microscope in the same or similar fashion as the wavefront sensor in U.S. Pat. No. 7,883,505, filed Apr. 20, 2005, and entitled "INTEGRATED SURGICAL MICROSCOPE AND WAVEFRONT SENSOR," the entire contents of which are incorporated by reference herein. In some embodiments, the optical power measurement device 920 includes a housing with an optical passageway therethrough. A beam splitter, dichroic mirror, etc. can be positioned in the optical passageway of the housing. The optical power measurement device can also include a connector for attaching the device to, and removing the device from, the surgical microscope such that it is optically aligned with the surgical microscope. For example, the optical power measurement device 920 can be mounted beneath the objective lens of the surgical microscope such that the objective lens can receive light through the optical passageway through the measurement device 920. The beam splitter or dichroic mirror located in the optical power measurement device housing can, for example, direct infrared light to the optical components of the measurement device 920, while transmitting visible light to the objective lens of the surgical microscope. In some embodiments, the optical power measurement device 920 and the surgical microscope may not share a lens. In other embodiments, the optical power measurement device 920 and the surgical microscope may share a lens, but the optical power measurement device 920 may not substantially compromise the focal length of the surgical microscope.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps may be altered, added, removed, or rearranged in ways that will be appreciated by those of ordinary skill in the art.

The foregoing disclosure has partitioned devices and systems into multiple components or modules for ease of explanation. The components or modules may be embodied as computer hardware (e.g., processors, volatile or non-volatile memories, circuit boards, chipsets, etc.). It is to be understood, however, that one or more components or modules may operate as a single unit. Conversely, a single component or module may comprise one or more sub-components or sub-modules. Further, the communication between components or modules may occur in a variety of ways, such as hardware implementations (e.g., over a network, serial interface, parallel interface, or internal bus), software implementations (e.g., database, passing variables), or a combination of hardware and software. Such communications can use a variety of signals, protocols, and standards. In addition, where methods are described that are, or could be, at least in part carried out by computer software, it should be understood that such methods can be provided on computer-readable media (e.g., optical disks such as CDs or DVDs, hard disk drives, flash memories, diskettes, or the like) that, when read by a computer or other processing device, cause it to carry out the method.

The systems and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. An ophthalmic optical power measurement device comprising:
   a light source configured to direct an input beam of light into the eye of a patient;
   an aperture configured to receive an output beam of light from the eye, the output beam of light comprising light from the input beam that scatters from a location on the retina of the eye and exits through the pupil of the eye;
   a detector configured to receive the output beam after it has passed through the aperture; and
   a processor configured to determine the size of a spot created by the output beam on the detector, and to determine the optical power of the eye based upon a relationship between the size of the spot, the size of the aperture, and the distance between the aperture and the detector,
   wherein the device has substantially zero optical power from the aperture to the detector.

2. The ophthalmic optical power measurement device of claim 1, wherein the processor is configured to measure a width of the spot taken along at least one axis, and to determine the optical power of the eye based upon the width of the spot along the axis.

3. The ophthalmic optical power measurement device of claim 2, wherein the optical power comprises the spherical power of the eye.

4. The ophthalmic optical power measurement device of claim 2, wherein the processor is configured to measure a plurality of widths of the spot taken along a plurality of axes, and to determine the optical power of the eye based upon the plurality of widths of the spot along the respective plurality of axes.

5. The ophthalmic optical power measurement device of claim 4, wherein the optical power comprises the spherical and cylindrical power of the eye.

6. The ophthalmic optical power measurement device of claim 1, wherein the processor is configured to determine the optical power of the eye based only upon the size of the spot on the detector.

7. The ophthalmic optical power measurement device of claim 1, wherein the aperture is dynamically adjustable, and wherein the processor is configured to control the size of the aperture to transmit only a portion of the output beam that exits through a desired analysis region of the pupil of the eye.

8. The ophthalmic optical power measurement device of claim 7, wherein the desired analysis region of the pupil of the eye comprises a central circular portion of the pupil with about a 4 mm diameter.

9. The ophthalmic optical power measurement device of claim 1, further comprising one or more optical components configured to relay the output beam from the eye to the aperture.

10. The ophthalmic optical power measurement device of claim 9, wherein the one or more optical components comprise a lens whose conjugate planes are located at approximately the exit pupil of the eye and the aperture, when the ophthalmic optical power measurement device is located at a desired spatial location with respect to the eye.

11. The ophthalmic optical power measurement device of claim 10, wherein the aperture has a fixed size.

12. The ophthalmic optical power measurement device of claim 1, further comprising an alignment system for positioning the optical power measurement device at a desired spatial location with respect to the eye.

13. The ophthalmic optical power measurement device of claim 1, wherein the optical power measurement device is integrated with a surgical microscope.

14. The ophthalmic optical power measurement device of claim 13, wherein the surgical microscope is suitable for performing cataract surgeries.

15. The ophthalmic optical power measurement device of claim 1, wherein the optical power measurement device is a handheld device.

16. The ophthalmic optical power measurement device of claim 1, wherein the optical power measurement device has a dynamic range suitable for measuring the phakic, pseudophakic, or aphakic optical power of the eye.

17. The ophthalmic optical power measurement device of claim 16, wherein the dynamic range of the optical power measurement device is at least about −5.0 Diopters to about +20.0 Diopters.

18. The ophthalmic optical power measurement device of claim 1, wherein the processor is further configured to determine the power of a suitable intraocular lens for the patient based upon a measurement of aphakic optical power of the eye.

19. The ophthalmic optical power measurement device of claim 1, wherein the detector comprises an array of electronic sensors or a diffuse surface and a camera configured to image the diffuse surface.

20. The ophthalmic optical power measurement device of claim 1, wherein the light source comprises a laser or a super luminescent diode.

21. The ophthalmic optical power measurement device of claim 1, wherein the input beam is collimated.

22. The ophthalmic optical power measurement device of claim 1, wherein the input beam has a diameter of 1 mm or less.

* * * * *